(12) United States Patent
Fan et al.

(10) Patent No.: US 12,247,916 B2
(45) Date of Patent: Mar. 11, 2025

(54) IDENTIFICATION METHOD OF PLASTIC MICROPARTICLES

(71) Applicant: National Taiwan University, Taipei (TW)

(72) Inventors: Chihhao Fan, Taipei (TW); Jhen-Nan Lin, Taipei (TW); Jun-Wei Li, Taipei (TW); Ya-Zhen Huang, Taipei (TW)

(73) Assignee: National Taiwan University, Taipei (TW)

( * ) Notice: Subject to any disclaimer, the term of this patent is extended or adjusted under 35 U.S.C. 154(b) by 38 days.

(21) Appl. No.: 17/833,936

(22) Filed: Jun. 7, 2022

(65) Prior Publication Data

US 2023/0228678 A1 Jul. 20, 2023

(30) Foreign Application Priority Data

Jan. 17, 2022 (TW) .................................. 111101852

(51) Int. Cl.
| | | |
|---|---|---|
| *G01N 33/00* | (2006.01) | |
| *G01J 3/42* | (2006.01) | |
| *G01N 21/3563* | (2014.01) | |
| *G01N 33/44* | (2006.01) | |
| *G01J 3/28* | (2006.01) | |
| *G01N 21/35* | (2014.01) | |

(52) U.S. Cl.
CPC ............ *G01N 21/3563* (2013.01); *G01J 3/42* (2013.01); *G01N 33/442* (2013.01); *G01J 2003/2859* (2013.01); *G01N 2021/3595* (2013.01)

(58) Field of Classification Search
CPC ............ G01N 21/3563; G01N 33/442; G01N 2021/3595; G01J 3/42; G01J 2003/2859
See application file for complete search history.

(56) References Cited

U.S. PATENT DOCUMENTS

| | | | | |
|---|---|---|---|---|
| 5,510,619 A | * | 4/1996 | Zachmann | ......... G01N 21/3563 250/339.08 |
| 2017/0336264 A1 | * | 11/2017 | Chanda | .............. G01N 21/3563 |
| 2023/0314314 A1 | * | 10/2023 | Michel | ............... G02B 27/0006 250/341.1 |

FOREIGN PATENT DOCUMENTS

| | | | | |
|---|---|---|---|---|
| WO | WO-2019171312 A1 | * | 9/2019 | ............... G01N 1/34 |
| WO | WO-2021231396 A1 | * | 11/2021 | |

OTHER PUBLICATIONS

Jung et al., Validation of ATRFT-IR to identify polymers of plastic marine debris, including those ingested by marineorganisms, 2018, Marine Pollution Bulletin, vol. 127, pp. 704-716. (Year: 2018).*

(Continued)

*Primary Examiner* — Dani Fox
*Assistant Examiner* — Miya Downing
(74) *Attorney, Agent, or Firm* — Amin, Turocy & Watson, LLP

(57) ABSTRACT

Provided is an identification method of plastic microparticles, including: performing an infrared analysis on plastic microparticles to identify whether the plastic microparticles include polyethylene terephthalate, polyethylene, polypropylene, or nylon 66, wherein the identification is to determine whether the plastic microparticles have a characteristic peak of each plastic, and the characteristic peak is selected from signals that do not overlap and interfere with each other in the infrared spectrum signals of each plastic.

5 Claims, 14 Drawing Sheets

(56) References Cited

OTHER PUBLICATIONS

Konechnaya et al., Optimized micro plastic analysis based on size fractionation, density separation and µ-FTIR, 2020, , Water Science and Technology, vol. 81, pp. 1-11 (Year: 2020).*

Fuller et al., A Procedure for Measuring Microplastics using Pressurized Fluid Extraction, 2016, Environ. Sci., Technology, vol. 50, pp. 5774-5780. (Year: 2016).*

Yuan et al., Angular Characterization of Polymer Surfaces by FTIR ATR dichroism with a rotatable truncated hemispheric crystal., 1991, Macromolecules, vol. 24, pp. 6095-6103. (Year: 1991).*

Umamaheswari et al., FTIR spectroscopic study of fungal degradation of poly(ethylene terephthalate) and polystyrene foam, 2013, Elixir Chem. Engg., vol. 64, pp. 19159-19164. (Year: 2013).*

Lv et al., Discrimination of Carbonate-Containing and Carbonate-Free Polyvinyl Chloride with Fourier Transform, Jun. 2012, Spectroscopy vol. 27 pp. 36-41. (Year: 2012).*

Fan, et al. "Microplastic constituent identification from admixtures by Fourier-transform infrared (FTIR) spectroscopy: The use of polyethylene terephthalate (PET), polyethylene (PE), polypropylene (PP), polyvinyl chloride (PVC) and nylon (NY) as the model constituents" Environmental Technology & Innovation, 23, 101798, Jul. 16, 2021.

Yu, et al. "Characterization of microplastics in environment by thermal gravimetric analysis coupled with Fourier transform infrared spectroscopy" Marine pollution bulletin, 145, 153-160, 2019.

Olesen, et al. "Microplastics in a stormwater pond" Water, 11(7), 1466, 2019.

Huang, et al. "Microplastic accumulation in fish from Zhanjiang mangrove wetland, South China" Science of The Total Environment, 708, 134839, 2020.

Araujo, et al. "Identification of microplastics using Raman spectroscopy: Latest developments and future prospects" Water research, 142, 426-440, 2018.

Geyer, et al. "Production, use, and fate of all plastics ever made" Science advances, 3(7), e1700782, 2017.

* cited by examiner

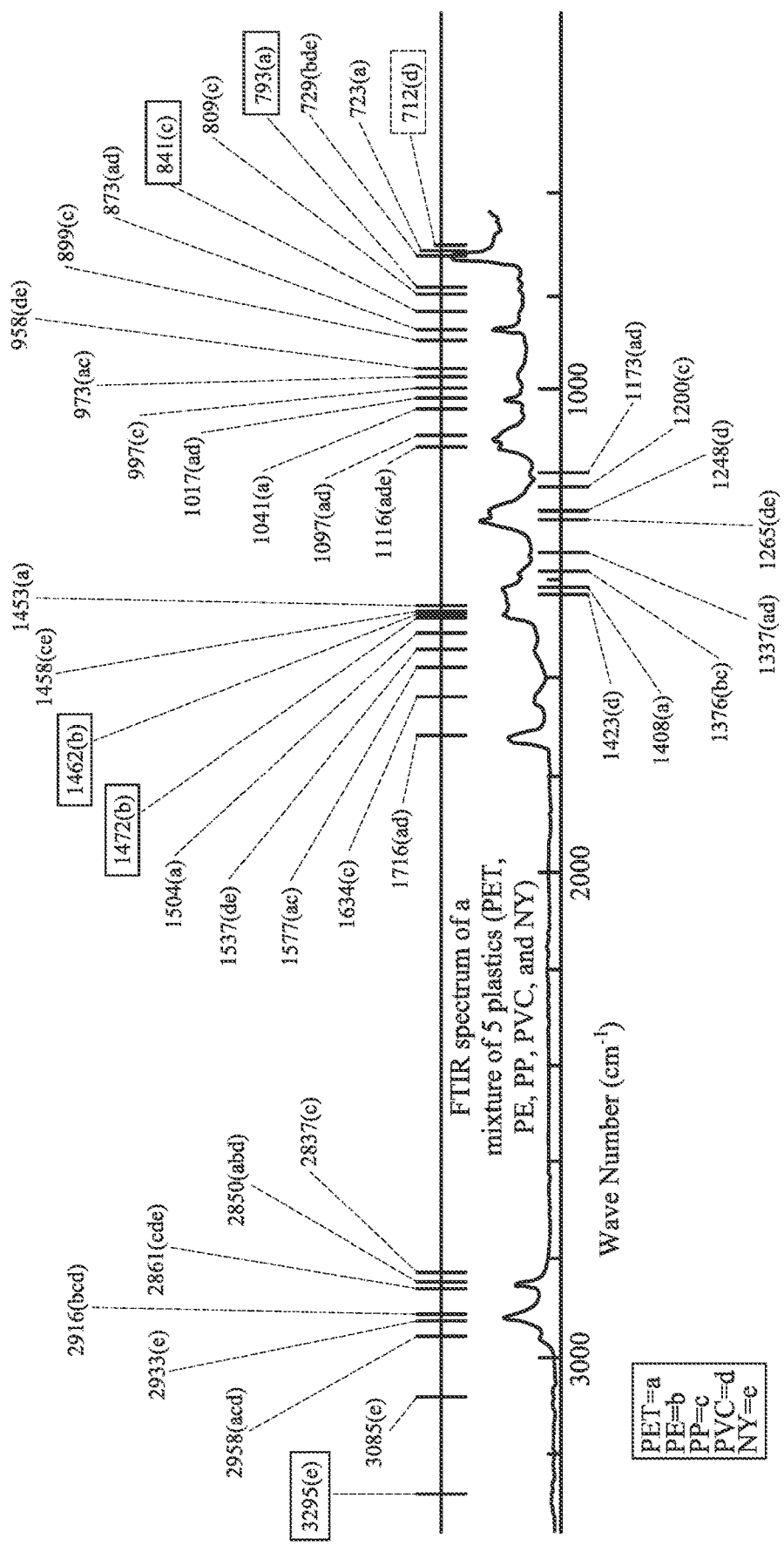

IDENTIFICATION METHOD OF PLASTIC MICROPARTICLES

CROSS-REFERENCE TO RELATED APPLICATIONS

This application claims priority to Taiwan Application Serial No. 111101852, filed on Jan. 17, 2022. The entirety of the application is hereby incorporated by reference herein and made a part of this application.

BACKGROUND

1. Technical Field

The present disclosure relates generally to an identification method of plastic microparticles, and more particularly, to a identification method of polyethylene terephthalate (PET), polyethylene (PE), polypropylene (PP), nylon 66 (NY) and other plastic constituents such as polyvinyl chloride (PVC).

2. Description of Related Art

According to a study by Geyer et al. 2017, in the total amount of global plastic production, PE accounts for 36%, PP accounts for 21%, PVC accounts for 12%, followed by each of polyethylene terephthalate (PET), polyurethane (PUR), and polystyrene (PS) accounts for less than 10%), and these groups of plastics account for more than 92% of all plastics generated worldwide. Fiber-based plastic Nylon is also a plastic product widely used by humans. These plastic products are used extensively and discarded as waste in the environment, and in combination with weathering over the years, the structure progressively breaks down into plastic microparticles. Such plastic microparticles remain in various environments and drift throughout the drinking water, rivers, lakes, and oceans through circulation, causing adverse impacts on the environment, organisms, and especially humans.

Various assessment methods and analytical procedures have been used in previously published literature to detect plastic microplastics. For example, Yu et al. (2019) use TGA-FTIR to quantify the plastic microparticles of PVC and PS; Olesen et al. (2019) use FPA-µFTIR for distribution imaging and automated data analysis of plastic microparticles in a reservoir; Huang et al. (2020) use micro-FTIR to investigate the size and content of plastic microparticles in mangrove wetland, and to identify accumulation of plastic microparticles in fish in this environment; and Araujo et al. (2018) use Raman spectroscopy for composition analysis and imaging of the plastic microparticles in the environment.

From the aforementioned results of the researches, most detections of plastic microparticles are regardless of the plastic composition in the sample but focus on counting the number and weight of plastic microparticles based on the whole sample to show the amount of plastic microparticles. However, plastic microparticles may contain various types of plastic constituents. Each type of plastic constituent has its own unique physical and chemical properties due to differences in its molecular structure, and this results in not only varying degrees of threat to the environment, but also various errors caused during assessment and analysis. Accordingly, in order to correctly assess the impact of plastic microparticles on the environment and ecology, there is a need for a method capable of distinguishing and identifying various types of plastic constituents in the plastic microparticles.

The aforementioned research articles are as follows:

Geyer, R., Jambeck, J. R, and Law, K. L. 2017. Production, use, and fate of all plastics ever made. Science advances, 3(7), e1700782.

Yu, J., Wang, P., Ni, F., Cizdziel, J., Wu, D., Zhao, Q., and Zhou, Y. (2019). Characterization of microplastics in environment by thermal gravimetric analysis coupled with Fourier transform infrared spectroscopy. Marine pollution bulletin, 145, 153-160.

Olesen, K. B., Stephansen, D. A., van Alst, N. and Vollertsen, J. (2019). Microplastics in a stormwater pond. Water, 11(7), 1466.

Huang, J. S., Koongolla, J. B., Li, H. X., Lin, L., Pan, Y. F., Liu, S., and Xu, X. R. (2020). Microplastic accumulation in fish from Zhanjiang mangrove wetland, South China. Science of The Total Environment, 708, 134839.

Araujo, C. F., Nolasco, M. M., Ribeiro, A. M., and Ribeiro-Claro, P. J. 2018. Identification of microplastics using Raman spectroscopy: Latest developments and future prospects. Water research, 142, 426-440.

SUMMARY

In view of this, the present disclosure provides an identification method of plastic microparticles, including: performing an infrared analysis on the plastic microparticles to identify whether the plastic microparticles include at least one plastic selected from the group consisting of PET, PE, PP and NY, wherein the identification is to determine whether the plastic microparticles have characteristic peaks of each of the at least one plastic, and the characteristic peaks are selected from signals that do not overlap and interfere with each other among infrared spectral signals of each of the at least one plastic.

In an embodiment, the characteristic peak of PET is at $793\pm5$ cm$^{-1}$, the characteristic peaks of PE are at $1472\pm5$ cm$^{-1}$ and $1462\pm5$ cm$^{-1}$, and the characteristic peak of PP is at $841\pm5$ cm$^{-1}$ and the characteristic peak of NY is at $3295\pm5$ cm$^{-1}$.

In an embodiment, the identification method of plastic microparticles of the present disclosure further includes performing pre-cleaning treatment on the plastic microparticles before performing the infrared analysis.

In an embodiment, the pre-cleaning treatment includes removing organics by Fenton reaction and rinsing the plastic microparticles with water.

In an embodiment, the identification method of plastic microparticles of the present disclosure further includes performing a pellet-forming pretreatment of the plastic microparticles with potassium bromide before performing the infrared analysis.

In an embodiment, the identification method of plastic microparticles of the present disclosure further includes performing solvent extraction on the plastic microparticles before performing the infrared analysis.

In an embodiment, the solvent extraction is performed with a solvent selected from a group consisting of tetrahydrofuran, nitrobenzene, cyclohexanone, dichloromethane, trichloromethane, and carbon tetrachloride.

In an embodiment, the identification method of plastic microparticles of the present disclosure further comprises forming crystals from the extract obtained by solvent extraction, and performing an infrared analysis on the crystals to further identify whether the plastic microparticles contain constituents other than PET, PE, PP and NY.

In an embodiment, the identification method of plastic microparticles of the present disclosure further includes identifying whether the plastic microparticles contain PVC.

In an embodiment, the characteristic peak of PVC is at 712±5 cm$^{-1}$.

BRIEF DESCRIPTION OF THE DRAWINGS

FIG. 2 is a FTIR spectrum of a plastic mixture comprising five types of plastics including PET, PE, PP, PVC and NY, wherein (a) represents the peak contributed by PET, (b) represents the peak contributed by PE, and (c) represents the peak contributed by PP, (d) represents the peak contributed by PVC, and (e) represents the peak contributed by NY.

DETAILED DESCRIPTION

Figure 1A:
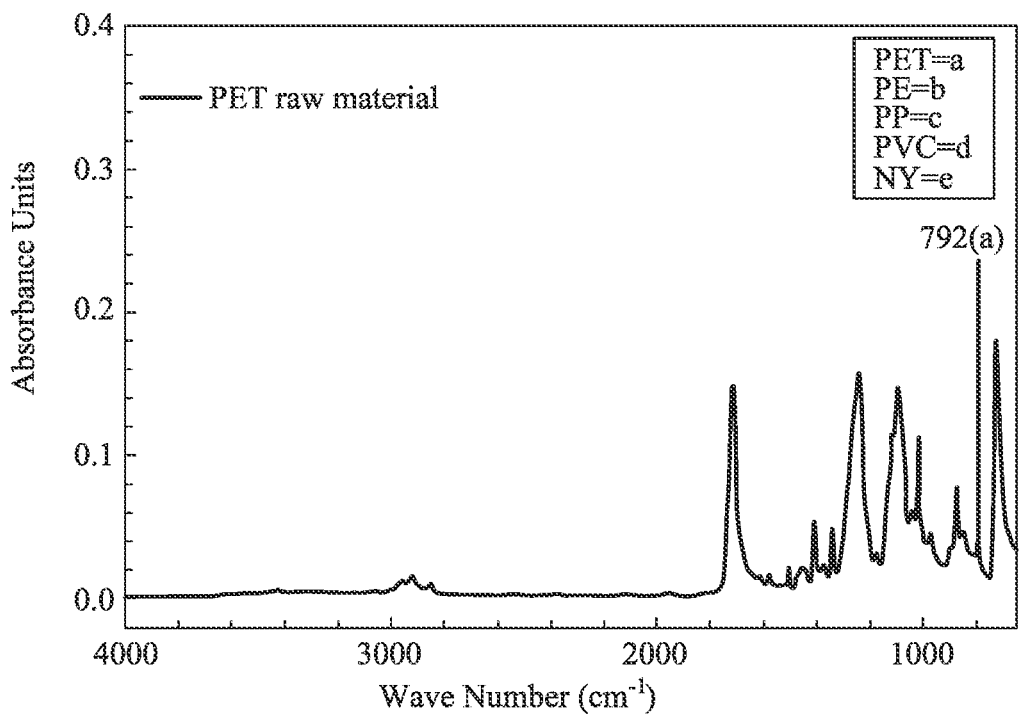
FIGS. 1A to 1E are Fourier-transform infrared spectroscopy (abbreviated as FTIR) spectra of PET, PE, PP, PVC and NY, respectively.

The embodiments of the present disclosure will be described below through specific embodiments, and those people with ordinary knowledge in the technical field can easily comprehend the scope and effect of the present disclosure based on the contents described herein. However, the specific embodiments described herein should not be construed as limiting the scope of the present disclosure. The listed technical features or solutions can be combined with each other. The present disclosure can also be implemented or applied through different embodiments. The details can also be given modifications or recombination according to different viewpoints and applications without departing from the scope and the spirit of the present disclosure.

Unless stated otherwise, the term "comprising," "including," "containing," or "having" particular elements used herein means that other elements such as units, components, structures, regions, parts, devices, systems, steps, or connection associations can be also included rather than excluded.

Unless expressly stated otherwise, the singular forms "a," "an," and "the" also include the plural forms, and the "or" and "and/or" can be used interchangeably herein.

The value ranges recited herein are inclusive and can be combined, and any value falling into the value range recited herein can be used as the upper or lower limit to derive a subrange; for example, a range of values "250 mesh or above" should be understood to include any sub-range from a minimum value of 250 mesh or above; for example, 250 mesh or above, 300 mesh or above, and 500 mesh or above, and etc. . . . . In addition, if a value range falls within each range described herein (e.g., 500 mesh falls into a range of 250 mesh or above), that is, the value should be deemed to be included in the scope of the present disclosure.

The present disclosure takes into account the lots of environmental impacts caused by the extremely large production and usage of PET, PE, PP, and NY, so it is particularly focused on identifying the constituents of PET, PE, PP and NY from unknown plastic microparticles. On the other hand, since PVC is also a widely used plastic, the present disclosure further provides an identification method of the constituents of PET, PE, PP, PVC and NY from unknown plastic microparticles. The present disclosure is characterized in that, unknown plastic microparticles can be identified in a single IR analysis to contain multiple plastic constituents without multiple and complicated steps of extraction and separation. The method is simple and fairly accurate.

In the field of material analysis and identification, infrared spectroscopy, such as Fourier-transform infrared spectroscopy (FTIR) is a widely used analytical technique. Different components respond differently to optical radiation due to differences in molecular structure. FTIR spectrometer establishes an infrared spectrum that corresponds to the specific component since different components have different degrees of absorption for each wavelength of infrared.

Figure 1B:
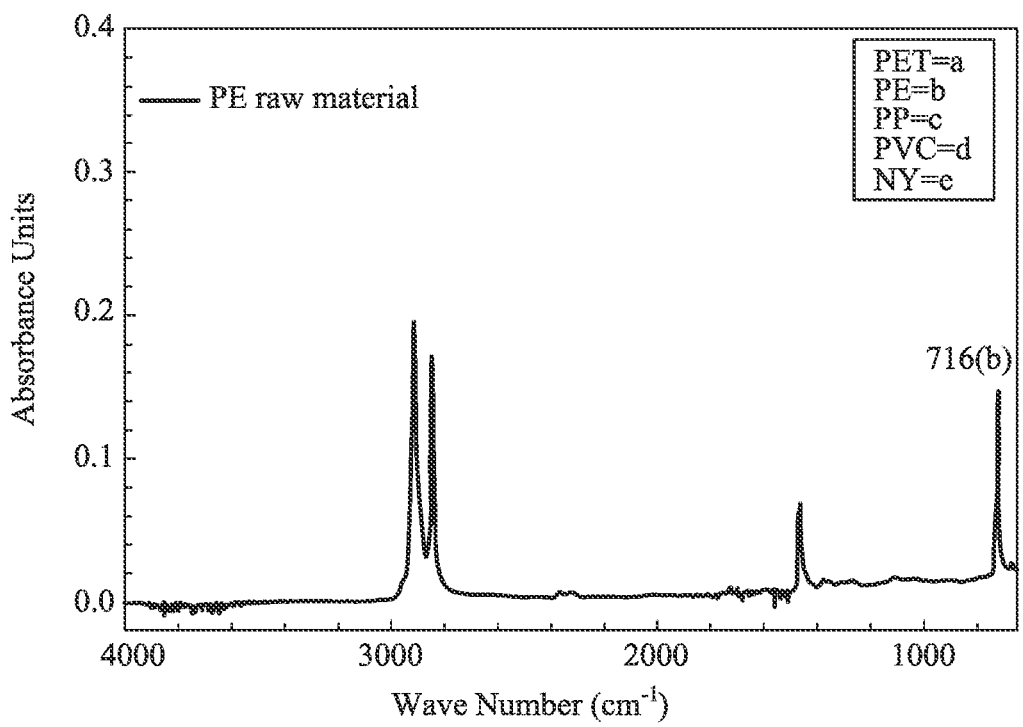
Figure 1C:
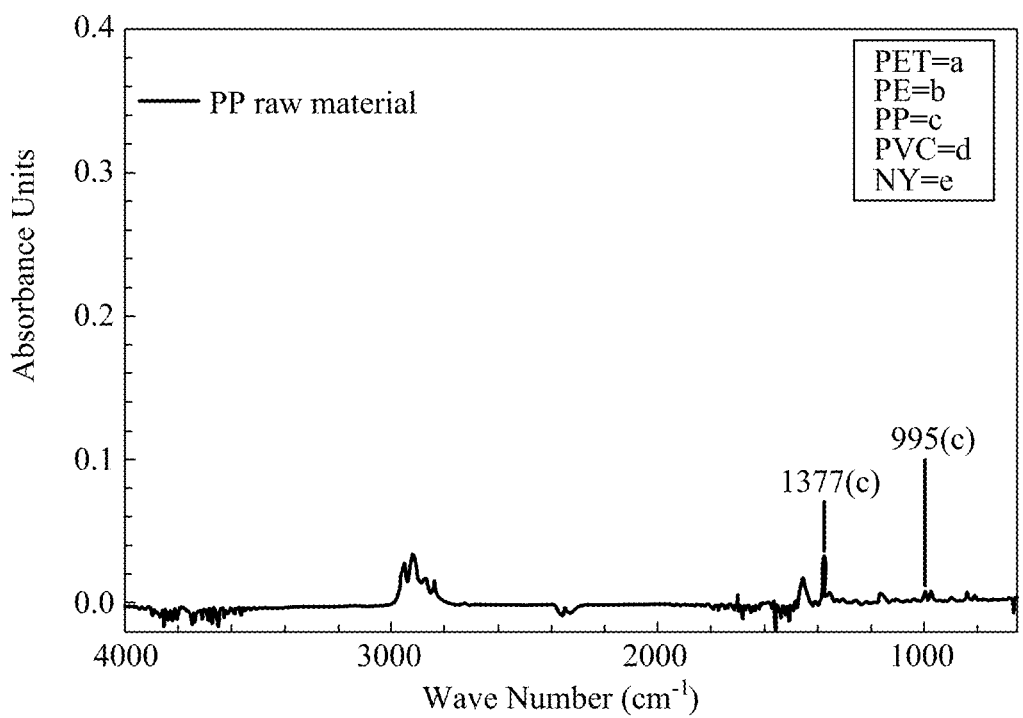
Figure 1D:
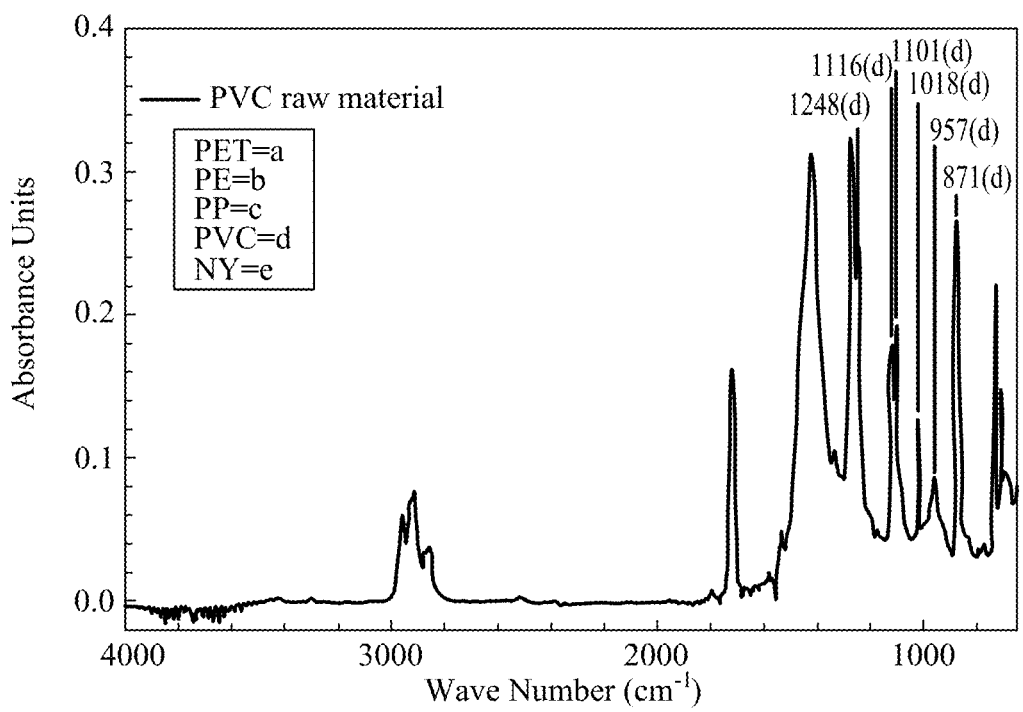
Figure 1E:
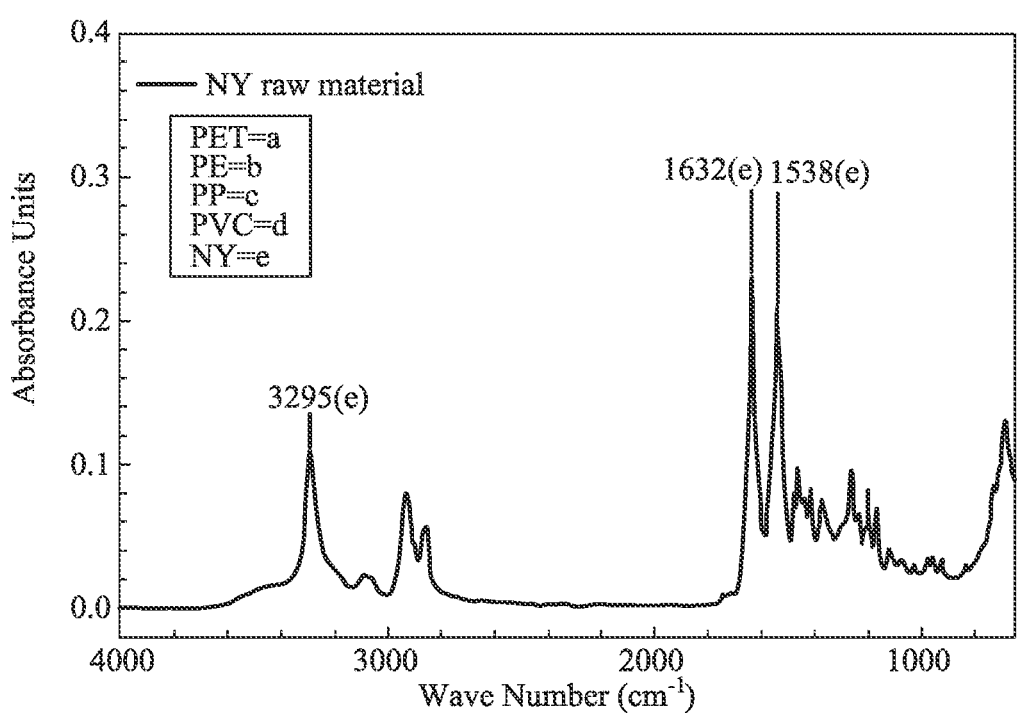

As shown in FIGS. 1A to 1E, common plastics, PET, PE, PP, PVC and NY, differ in its monomers and polymerization, therefore, each of them has its characteristic FTIR spectrum. According to FTIR spectrum, substances may have signals at the same wave number. When analyzing a sample with various types of plastics and other impurities, the plastics and impurities have different infrared absorptions and may interfere with each other to present hybrid, summed signals, leading to misinterpretations in determining what the sample contains. Therefore, for a mixture containing unknown components, the strong peak of a specific substance should not be directly interpreted as the characteristic peak for the identification, but the relatively strong peak should be selected as the characteristic peak after eliminating the signals that may interfere with each other. For example, the FTIR spectrum of PE as shown in FIG. 1B has peaks at 2916±5 cm$^{-1}$, 2850±5 cm$^{-1}$ and 716±5 cm$^{-1}$, but these peak may be interfered or masked by other plastics PET, PP, PVC, and NY (as shown in FIGS. 1A, 1C, 1D, and 1E). If a sample contains multiple constituents in the mixture, PE may not be directly identified based on the peaks at 2916±5 cm$^1$, 2850±5 cm$^{-1}$ and 716±5 cm$^{-1}$; on the contrary, in the identification method of plastic microparticles described in this disclosure, the characteristic peaks are determined by comparing the FTIR spectra of the various common types of plastics with each other and further confirmed by the FTIR spectra of different combinations of plastic such that the characteristic peaks of PE are two peaks at 1472±5 cm$^{-1}$ and 1462±5 cm$^{-}$, respectively. Although the intensities of these characteristic peaks of PE are lower than those at 2916±5 cm$^{-1}$, 2850±5 cm$^{-1}$ and 716±5 cm$^{-1}$ mentioned above, these characteristic peaks of PE are not easy to overlap with characteristic peaks of other plastics. Therefore, the identification method of plastic microparticles of the present disclosure can accurately identify whether plastic mixtures contain plastic constituents of PE, PET, PP, NY or a combination thereof in plastic mixtures containing at least one plastic selected from PE, PET, PP and NY. On the other hand, the present disclosure can also accurately identify whether plastic mixtures contain plastic constituents of PE, PET, PP, PVC, NY or a combination thereof in the mixture containing at least one plastic selected from PE, PET, PP, PVC and NY. Therefore, the present disclosure can also accurately identify whether an unknown plastic sample contains plastic constituents of PE, PET, PP, PVC, NY or a combination thereof.

The selection procedure of the present disclosure results in that the intensities of characteristic peaks are typically smaller than the known strongest peak. Thus, the characteristic peaks are not easy to identify when the range of the wave number set in the spectrum is broad, such as from 4000 cm$^{-1}$ to 650 cm$^{-1}$. There is a need to select a suitable narrower range according to the characteristic peaks, so as to improve the identification of the characteristic peaks and improve the accuracy of component identification. For example, the characteristic peaks of the PE of the present disclosure is selected as two peaks at 1472±5 cm$^{-1}$ and 1462±5 cm$^{-1}$, which can be clearly and accurately identified in a relatively narrow range of FTIR spectra, e.g., the characteristic peak of PE as mentioned above can be clearly seen in the range of 1550 cm$^{-1}$ to 1350 cm$^{-1}$.

As mentioned above, in order to identify the plastic constituents contained in the plastic microparticles, the present disclosure mixes five common plastics: PET, PE, PP, PVC and NY and form a pellet to obtain a plastic mixture, which is analyzed by using FTIR. The result is shown in FIG. 2. It can be found that most peaks are contributed by two or more plastic constituents and the specific plastic constituent is accurately identified only when strictly comparing and selecting the characteristic peaks. After the comparison and confirmation described in this disclosure, the characteristic peaks of PET is selected at 793 cm$^{-1}$, the characteristic peaks of PE are selected at 1472±5 cm$^{-1}$ and 1462±5 cm$^{-1}$, the characteristic peak of PP is selected at 841±5 cm$^{-1}$ and the characteristic peak of NY is selected at 3295±5 cm$^{-1}$. Further, the characteristic peak of PVC is selected at 712±5 cm$^{-1}$.

The present disclosure performs the following comparison and confirm procedures to establish an identification method of whether plastic mixture microparticle contains PET, PE, PP, and NY.

Figure 3:
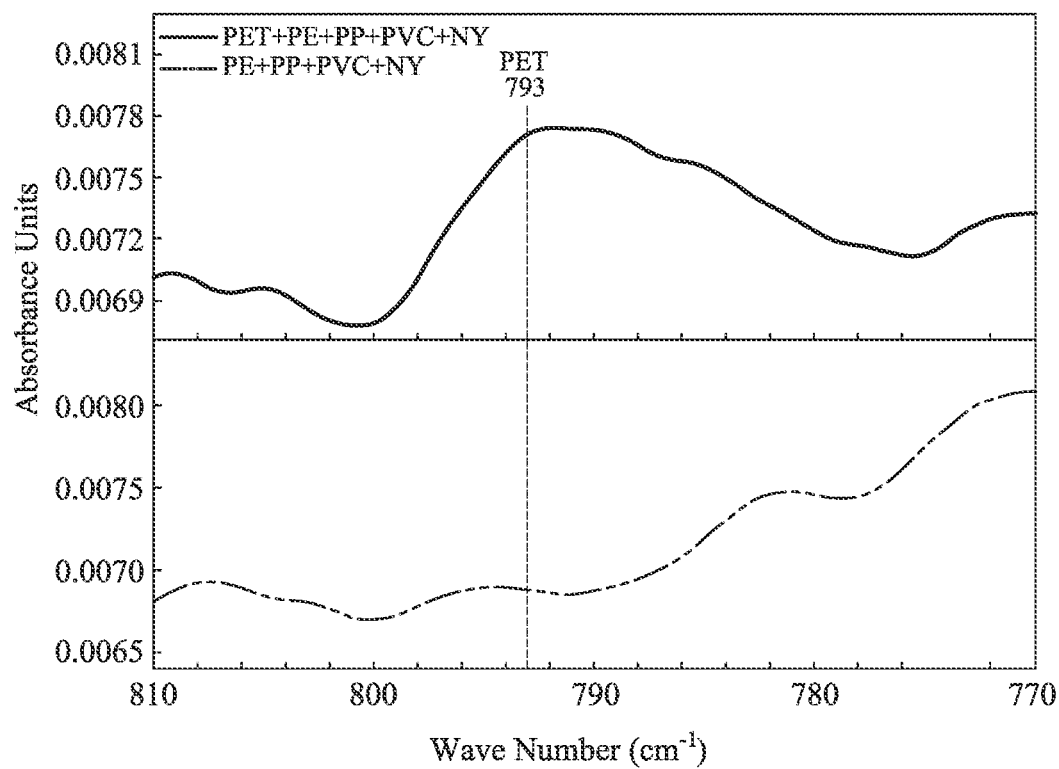
FIG. 3 is FTIR spectra of two plastic mixtures: one comprising five types of plastics including PET, PE, PP, PVC, and NY and the other comprising four types of plastics including PE, PP, PVC and NY.

As shown in FIG. 3, the present disclosure compared FTIR spectra of a plastic mixture mixed five plastics of PET, PE, PP, PVC and NY and a plastic mixture mixed four plastics of PE, PP, PVC and NY and observed that the plastic mixture mixed five plastics (including PET) has a clear peak at 793±5 cm$^{-1}$ compared with the plastic mixture mixed four plastics (excluding PET). It indicates this peak is contributed by PET and does not overlap and interfere with the peaks contributed by other plastics, so this peak can be selected as the characteristic peak of PET. However, the intensity of this peak is weak, so the range of the FTIR spectrum is set in a range of 890 cm$^{-1}$ to 690 cm$^{-1}$, or a narrower range of 840 cm$^{-1}$ to 740 cm$^{-1}$, 820 cm$^{-1}$ to 760 cm$^{-1}$, or 810 cm$^{-1}$ to 770 cm$^{-1}$ in order to more precisely identify the characteristic peak of PET.

Figure 4:
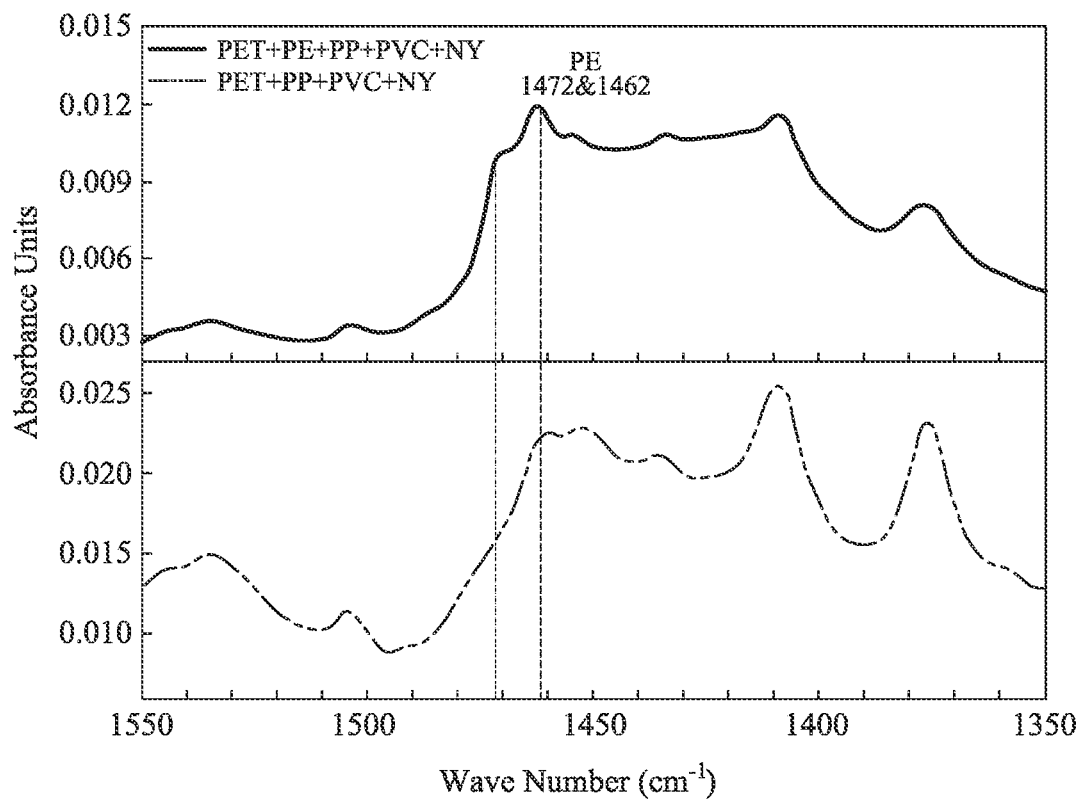
FIG. 4 is FTIR spectra of two plastic mixtures: one comprising five types of plastics including PET, PE, PP, PVC, and NY and the other comprising four types of plastics including PET, PP, PVC and NY.

As shown in FIG. 4, the present disclosure compared FTIR spectra of a plastic mixture mixed five plastics of PET, PE, PP, PVC and NY and a plastic mixture mixed four plastics of PET, PP, PVC and NY, and observed that the plastic mixture mixed five plastics (including PE) has two clear peaks at 1472±5 cm$^{-1}$ and 1462±5 cm$^{-1}$ compared with the plastic mixture mixed four plastics (excluding PE). It indicates these two peaks are contributed by PE and do not overlap and interfere with the peaks contributed by other plastics, so these two peaks can be selected as the characteristic peaks of PE. However, the intensities of these peaks are weak, so the range of the FTIR spectrum is set in a range of 1550 cm$^{-1}$ to 1350 cm$^{-1}$, or a narrower range of 1500 cm$^{-1}$ to 1400 cm$^{-1}$, 1520 cm$^{-1}$ to 1420 cm$^{-1}$, 1490 cm$^{-1}$ to 1430 cm$^{-1}$, or 1480 cm$^{-1}$ to 1440 cm$^{-1}$ in order to more precisely identify the characteristic peaks of PE.

Figure 5:
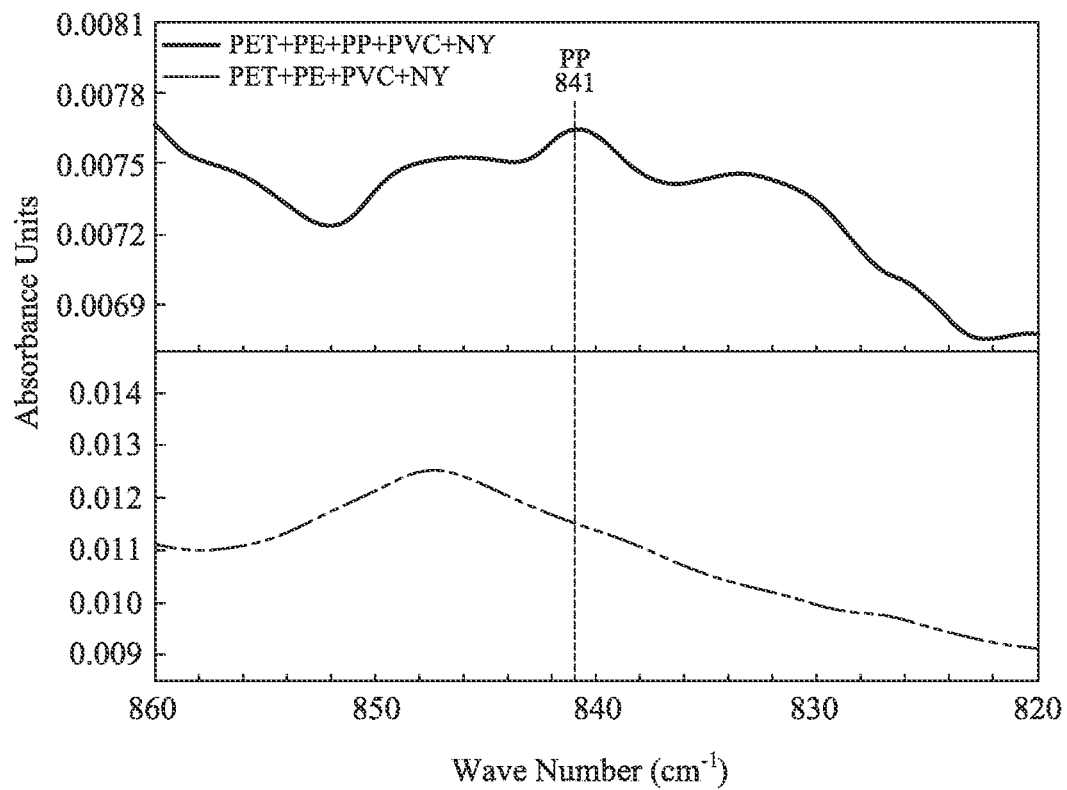
FIG. 5 is FTIR spectra of two plastic mixtures: one comprising five types of plastics including PET, PE, PP, PVC, and NY and the other comprising four types of plastics including PET, PE, PVC and NY.

As shown in FIG. 5, the present disclosure compared FTIR spectra of a plastic mixture mixed five plastics of PET, PE, PP, PVC and NY and a plastic mixture mixed four plastics of PET, PE, PVC and NY and observed that the plastic mixture mixed five plastics (including PP) has a significant peak at 841±5 cm$^{-1}$ compared with the plastic mixture mixed four plastics (excluding PP). It indicates that this peak is contributed by PP and does not overlap and interfere with the peaks contributed by other plastics, so this peak can be selected as the characteristic peak of PP. However, the intensity of this peak is weak, so the range of the FTIR spectrum is set in a range of 940 cm$^{-1}$ to 740 cm$^{-1}$, or a narrower range of 890 cm$^{-1}$ to 790 cm$^{-1}$, 870 cm$^{-1}$ to 810 cm$^{-1}$, or 860 cm$^{-1}$ to 820 cm$^{-1}$ in order to more precisely identify the characteristic peak of PP.

Figure 7:
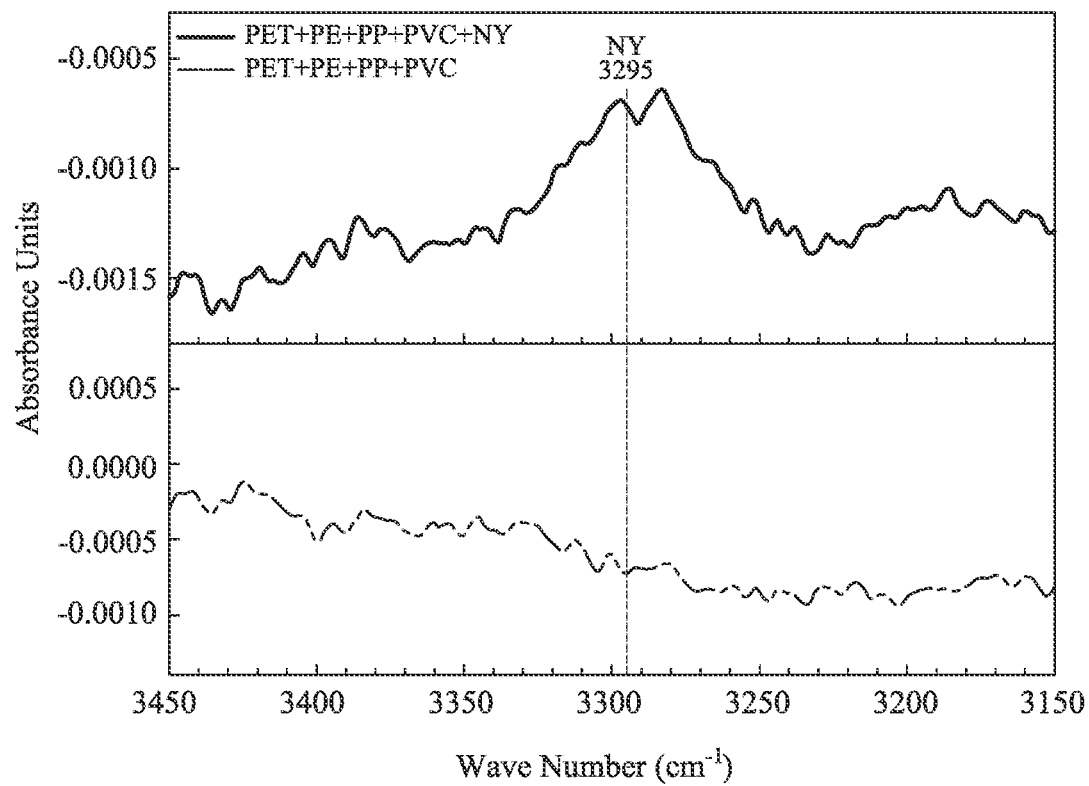
FIG. 7 is FTIR spectra of two plastic mixtures: one comprising five types of plastics including PET, PE, PP, PVC, and NY and the other comprising four types of plastics including PET, PE, PP and PVC.

As also shown in FIG. 7, the present disclosure compared FTIR spectra of a plastic mixture mixed five plastics of PET, PE, PP, PVC, and NY and a plastic mixture mixed four plastics of PET, PE, PP and PVC and observed that the plastic mixture mixed five plastics (including NY) exhibits a clear peak at 3295±5 cm$^{-1}$ compared with the plastic mixture mixed four plastic (excluding NY). It indicates that this peak is contributed by NY and does not overlap and interfere with the peaks contributed by other plastics, so this peak can be selected as the characteristic peak of NY. However, the intensity of this peak is weak, so the range of the FTIR spectrum is set in a range of 3450 cm$^{-1}$ to 3150 cm$^{-1}$, or a narrower range of 3400 cm$^{-1}$ to 3200 cm$^{-1}$, 3350 cm$^{-1}$ to 3250 cm$^{-1}$, or 3340 cm$^{-1}$ to 3260 cm$^{-1}$ in order to more precisely identify the characteristic peak of NY.

In addition to the above-mentioned identification method of whether the plastic mixture microparticles contain plastic PET, PE, PP and NY, the present disclosure also provides a method for further identifying whether a plastic mixture microparticles contain PVC in an embodiment.

Figure 6:
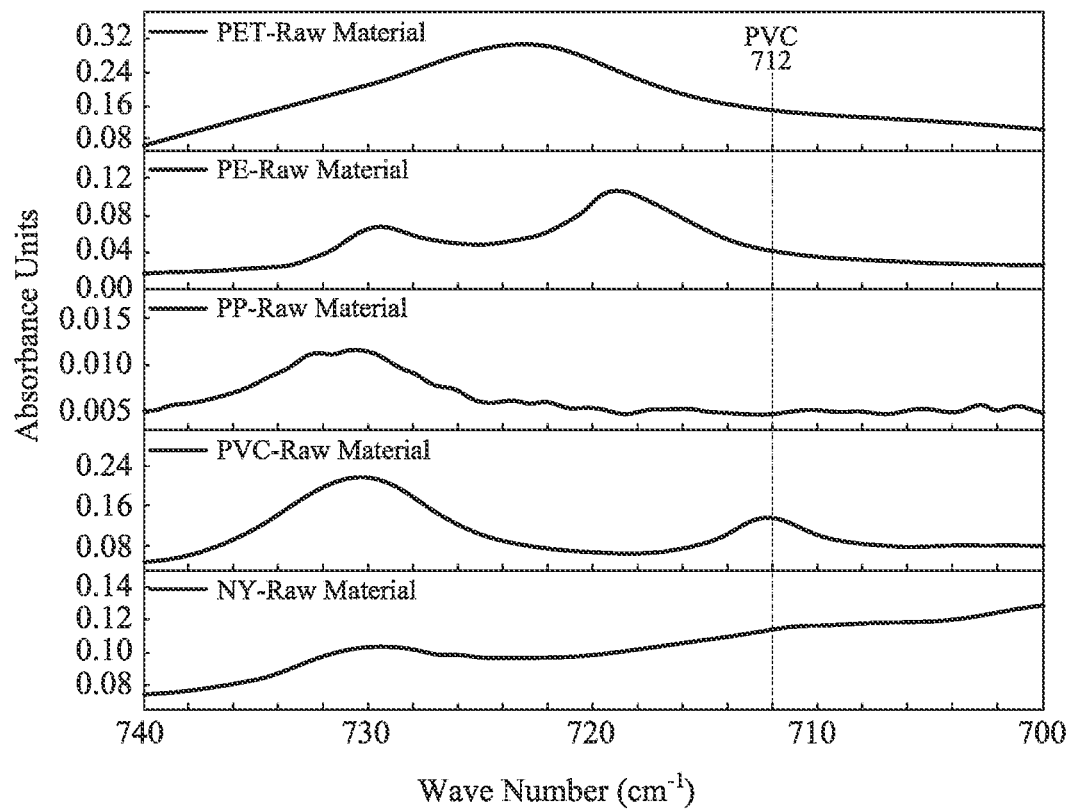
FIG. 6 is FTIR spectra of PET, PE, PP, PVC, and NY, respectively.

As shown in FIG. 6, the present disclosure compared FTIR spectra of individual plastics, such as PET, PE, PP, PVC and NY, and observed that PVC has a peak at 712±5 cm$^{-1}$ compared with other plastics, which can be selected as the characteristic peak of PVC. However, the intensity of this characteristic peak of PVC is weak, so the range of the FTIR spectrum is set in a range of 760 cm$^{-1}$ to 660 cm$^{-1}$, or a narrower range of 740 cm$^{-1}$ to 680 cm$^{-1}$, 730 cm$^{-1}$ to 690 cm$^{-1}$, or 720 cm$^{-1}$ to 700 cm$^{-1}$ in order to more precisely identify the characteristic peaks of PVC.

The present disclosure finds that the signal intensities of characteristic peaks of some plastics are weak, so in an embodiment, solvent extraction is performed on the samples before an infrared analysis to extract specific plastic constituent. For example, in an embodiment, the signal intensity of the selected characteristic peak is relatively low which may be easily interfered and masked by other constituents, so plastic microparticles are first extracted with a solvent selected from a group consisting of tetrahydrofuran, nitrobenzene, cyclohexanone, dichloromethane, trichloromethane and carbon tetrachloride, and then filtered. The extracted plastic microparticles continue to the next step of an infrared analysis, whereas the extract liquid is crystallized to obtain the plastic and the plastic is identified by an infrared analysis. In an embodiment, the characteristic peak of PVC, which is at 712±5 $cm^{-1}$, possess lower intensities, so the plastic mixture of mixed PET, PE, PP, PVC and NY is first extracted with tetrahydrofuran, and then the extracted plastic mixture is subjected to the next step of an infrared analysis. On the other hand, the extract liquid can go through crystallization to obtain PVC and the crystallized PVC is identified by an infrared analysis. Therefore, the present disclosure confirms that such a step of extraction of PVC in advance can be applied to the identification method of whether unknown plastic mixture microparticles contain PVC.

As mentioned above, the identification method of plastic microparticles of the present disclosure includes performing an infrared analysis on the plastic microparticles to identify whether the plastic microparticles contain a specific plastic constituent. The identification is to determine whether the plastic microparticles has characteristic peaks of each type of plastics, and the characteristic peaks are selected from the signals that do not overlap and interfere with each other in the infrared spectral signals of the respective plastics.

In an embodiment, before the infrared analysis, a step of pre-cleaning treatment may be applied on the plastic microparticles. The pre-cleaning treatment includes removing organics by Fenton reaction, and may also include rinsing the plastic microparticles with water. Pre-cleaning treatment may eliminate the interference of organics and impurities on the FTIR spectrum.

Fenton reaction conventionally uses ferrous ions ($Fe^{2+}$) and hydrogen peroxide ($H_2O_2$) as reagents, wherein ferrous ions and hydrogen peroxide react in solution to produce free hydroxyl radicals ($HO^-$) and perhydroxyl radicals ($HOO^-$), so these free radicals can be applied to oxidatively decompose organic pollutants on plastic microparticles. Other improved technologies based on the conventional Fenton reaction, such as photo-Fenton processes, electro-Fenton process, photoelectro-Fenton, sono-Fenton process, and Fenton-like reaction of Advanced Oxidation Processes (AOPs), are also included in the pretreatment steps of the Fenton process of the present disclosure.

In an embodiment, the plastic microparticles are pretreated to form a pellet with potassium bromide before the infrared analysis. Since the dimension of the plastic microparticles remaining in the environment (e.g., water sources) are small, similar to the dimension of ground powder, and usually the amount of samples collected at one time is very limited. Therefore, a small amount of plastic microparticles can be mixed with potassium bromide (KBr) powder or be ground optionally, and the mixture is placed in a pellet press machine to make a transparent pellet under a pressurized, vacuum condition in order to facilitate the infrared analysis.

In other embodiments, other sample preparation methods for IR analysis can also be applied, for example, the Nujol method is by mixing a liquid such as paraffin oil with the sample powder and coating on a salt plate for measurement; the solution method is by dissolving the sample in a solvent and the liquid with the dissolved sample is used directly for measurement; or the thin film method is by melting or dissolving the sample in a solvent to form a thin film for measurement.

In an embodiment, the particle sizes of the plastic microparticles suitable for analysis is 250 mesh or above, 300 mesh or above, 500 mesh or above, for example, 250 mesh, 300 mesh, 400 mesh, 500 mesh, or 600 mesh.

Figure 8:
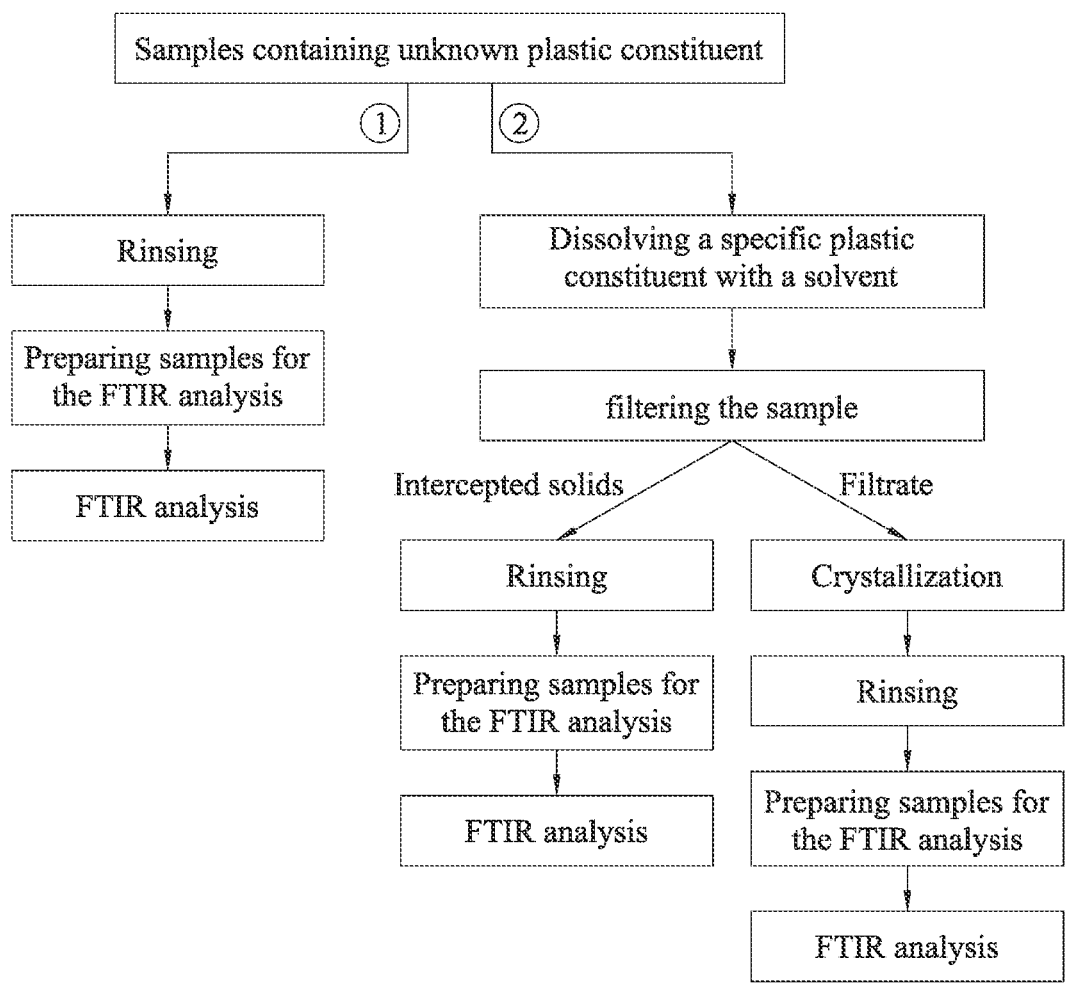
FIG. 8 is a flow chart of the identification method of plastic microparticles of the present disclosure.

According to the present disclosure, a simple flowchart of the identification method of plastic microparticles can be established, as shown in FIG. 8. For samples of unknown plastic composition, the identification of the plastic microparticlesample can be carried out via path ①. First, performing a pre-cleaning treatment depending on the degree of contamination of the sample. For pre-cleaning treatment, please refer to the above-mentioned description. Then, in order to facilitate infrared analysis, the sample needs to be prepared as that suitable for FTIR analysis, and the sample preparation can also refer to the above-mentioned description. In the embodiment of the present disclosure, potassium bromide is used to form a pellet. Finally, the sample can be subjected to FTIR analysis, and this FTIR analysis is performed after the above-mentioned selection of the characteristic peaks. It can be identified whether the sample contains the specific plastic constituents by determining whether the FTIR spectrum of the sample exhibit the selected characteristic peaks of the specific plastic thereby. On the other hand, samples of unknown plastic composition can also be identified via path ② for plastic microparticles. The difference between path ① and path ② is that the sample in path ② is subjected to solvent extraction before a step of rinsing. The solvent extraction is as described above, in which the sample is immersed in the solvent, sufficiently stirred and mixed to dissolve the specific plastic constituents in the solvent, and then filtered. The intercepted solid part (the plastic that is not dissolved in the solvent) is proceeded to the same steps as in path ①, while the solvent in the filtrate part (the plastic dissolves in the solvent) is volatilized, the dissolved plastic is crystallized, and then proceeded to the same steps as in path ①.

The present disclosure will be described in further detail with reference to the following examples, which are by no means intended to limit the scope of the present disclosure.

Example 1

Samples were collected from ambient surface water bodies in National Taiwan University (NTU). The samples were collected from the test water reservoir (A1) connected to the Hydrotech Research Institute, NTU, the water supply pipes (A2 and A3) connected to the reservoir, and a long and narrow ecological pool (B1) next to an experimental farmland. The samples were drawn from the water bodies with a water pump (model: SHIN KOMI 2HP) and the suspended microparticles were collected by filtration with a nylon filter with a pore size of 500 mesh (25 μm). The impurities were separated by the gravimetric method and collected in a 500 mL conical flask. The sample amounts of A1, A2, A3 and B1 were 2 mg, 4 mg, 6 mg, and 2 mg, and the concentrations in the sampling water were 8.0 ppb, 2.2 ppb, 3.0 ppb, and 1.0 ppb, respectively.

20 mL of tetrahydrofuran was added to the conical flask and stirred for extraction, and then the solution was filtered through a 500 mesh nylon filter of a vacuum filter device, and then followed by the Fenton reaction. The Fenton reaction was carried out as follows: 5 mL of 1 M ferrous sulfate and 5 mL of 0.5 M, 30 wt % $H_2O_2$ solution were taken with a dropper and dropped on a nylon filter, and the Fenton reaction was repeated once again after 30 seconds of reaction. After that, the plastic microparticle sample on the nylon filter was rinsed with water, and then the plastic microparticle sample was transferred into a beaker, placed in an oven and dried at 75° C. On the other hand, the extract solution was placed in a fume hood to volatilize tetrahydrofuran for crystallization, followed by rinsing with water and drying. The obtained plastic microparticle sample was mixed with an appropriate amount of potassium bromide, and the mixture was made into a pellet by a pellet press machine for FTIR analysis.

Figure 9:
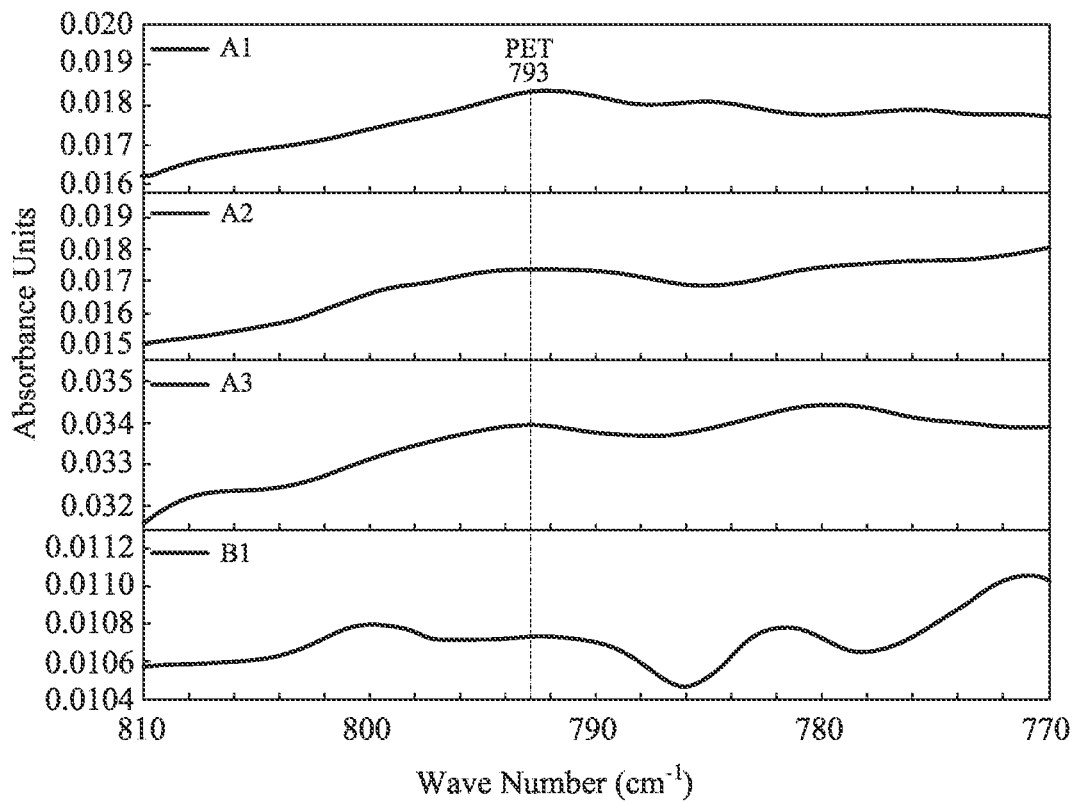
FIG. 9 is a comparison of the FTIR spectra of each sample in Example 1 of the present disclosure at the position of selected PET characteristic peaks.
Figure 10:
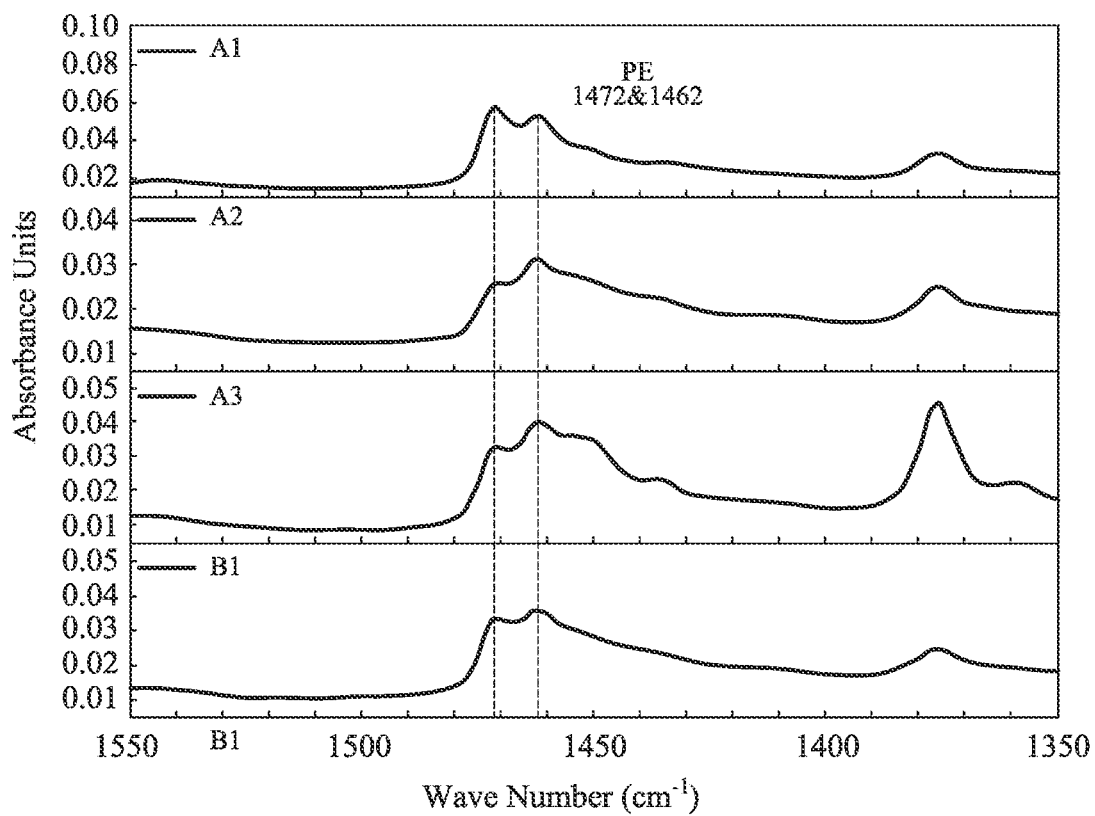
FIG. 10 is a comparison of the FTIR spectra of the samples in Example 1 of the present disclosure at the position of selected PE characteristic peaks.
Figure 11:
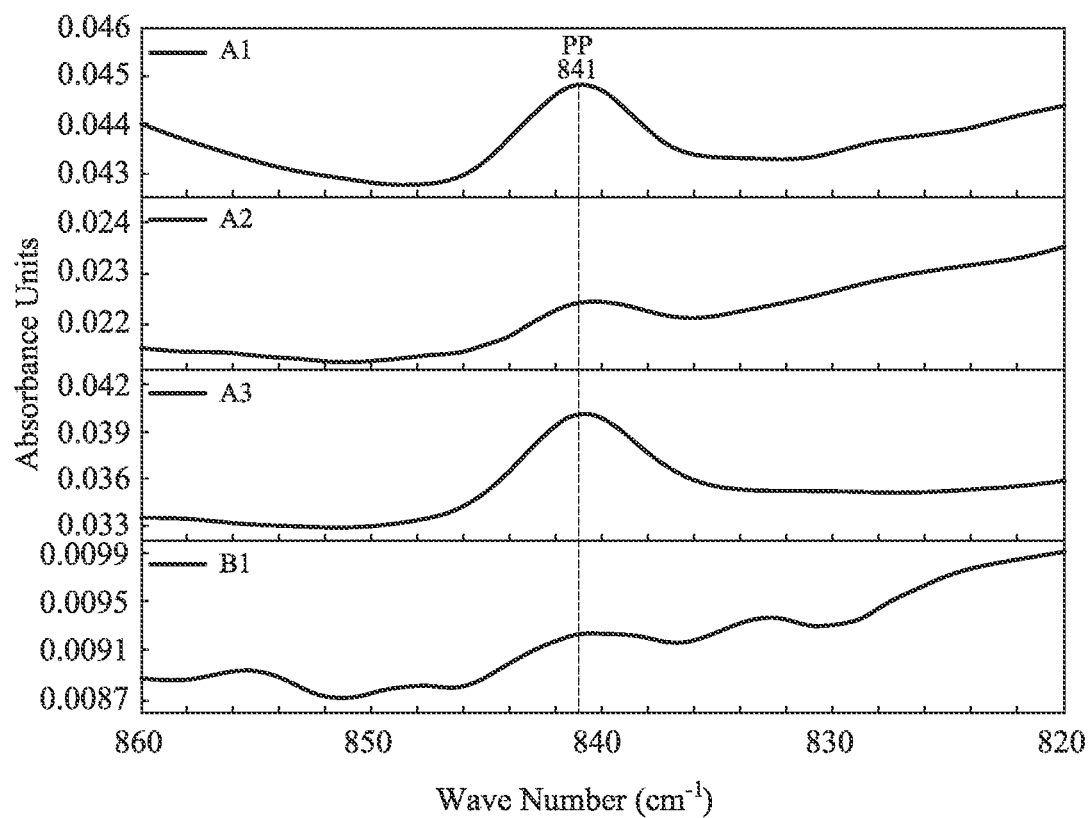
FIG. 11 is a comparison of the FTIR spectra of each sample in Example 1 of the present disclosure at the position of selected PP characteristic peak.
Figure 12:
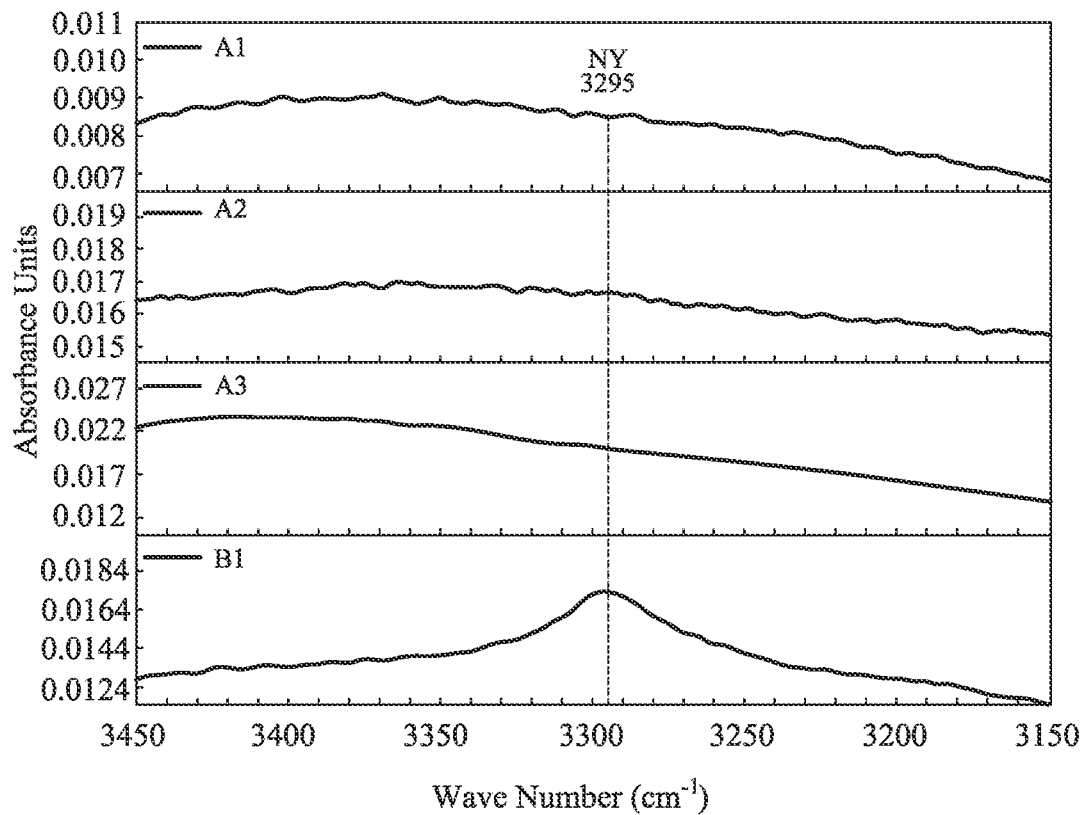
FIG. 12 is a comparison of the FTIR spectra of each sample in Example 1 of the present disclosure at the position of selected NY characteristic peak.

As shown in FIG. 9, the peak at 793±5 $cm^{-1}$ was identified in samples A1, A2 and A3, that is, the presence of characteristic peak of PET, and accordingly PET was identified in these samples A1, A2 and A3 and that the PET was not identified in sample B1. As shown in FIG. 10, the two peaks at 1472±5 $cm^{-1}$ and 1462±5 $cm^{-1}$ were identified in samples A1, A2, A3 and B1, that is, the presence of characteristic peaks of PE, and accordingly PE was identified in samples A1, A2, A3 and B1. As shown in FIG. 11, the peak at 841±5 $cm^{-1}$ was identified in samples A1, A2 and A3, that is, the presence of characteristic peak of PP and accordingly PP was identified in samples A1, A2 and A3. The spectrum of sample B1 was at 841±5 $cm^{-1}$, with no obvious peak and significantly lower absorbance than other signals, so it was determined that PP was not identified in sample B1. As shown in FIG. 12, the peak at 3295±5 $cm^{-1}$ was not identified in samples A1, A2 and A3, indicating that NY was not present in samples A1, A2 and A3; however, sample B1 showed a significant peak at 3295±5 $cm^{-1}$, that is, the presence of characteristics of NY, and thus, it was determined that NY was identified in sample B1. On the other hand, the results of the plastic obtained from the extract liquid showed that none of samples A1, A2, A3 and B1 contain PVC.

The results of this example showed that:
Sample A1 contains PET, PE, PP;
Sample A2 contains PET, PE, PP;
Sample A3 contains PET, PE, PP;
Sample B1 contains PE, NY;

Since the sampling areas of samples A1, A2 and A3 were the test water reservoirs and the water supply pipes that were connected to each other, the plastic microparticles have similar constituents. The sampling area of sample B1 was the long and narrow ecological pond next to the experimental farmland, so its plastic composition was significantly different from that of samples A1 to A3. Accordingly, the identification method of plastic microparticles of the present disclosure can effectively achieve the constituent identification of the unknown plastic microparticles.

What is claimed is:

1. An identification method of plastic microparticles, comprising:
    performing a solvent extraction on the plastic microparticles to extract a part of plastics; and
    performing an infrared analysis on the extracted plastic microparticles and crystals from an extract liquid obtained by the solvent extraction to identify whether the extracted plastic microparticles comprise at least one plastic selected from a group consisting of polyethylene terephthalate, polyethylene, polypropylene and nylon 66, and whether the crystals comprise polyvinyl chloride,
    wherein the identification is to determine whether the extracted plastic microparticles and the crystals have characteristic peaks of each of the at least one plastic, and the characteristic peaks are selected from signals that do not overlap and interfere with each other among infrared spectral signals of each of the at least one plastic,
    wherein the characteristic peak of the polyethylene terephthalate is at 793±5 $cm^{-1}$, the characteristic peaks of the polyethylene are selected as two peaks that do not overlap at 1472±5 $cm^{-1}$ and 1462±5 $cm^{-1}$, the characteristic peak of the polypropylene is at 841±5 $cm^{-1}$, the characteristic peak of the nylon is at 3295±5 $cm^{-1}$, and the characteristic peak of the polyvinyl chloride is at 712±5 $cm^{-1}$.

2. The method of claim 1, further comprising performing pre-cleaning treatment on the plastic microparticles prior to performing the infrared analysis.

3. The method of claim 2, wherein the pre-cleaning treatment comprises removing organics by Fenton reaction and rinsing the plastic microparticles with water.

4. The method of claim 1, further comprising a pellet-forming pretreatment of the plastic microparticles with potassium bromide prior to performing the infrared analysis.

5. The method of claim 1, wherein the solvent extraction is performed with a solvent selected from a group consisting of tetrahydrofuran, nitrobenzene, cyclohexanone, dichloromethane, trichloromethane and carbon tetrachloride.

* * * * *